United States Patent [19]

Cash

[11] Patent Number: 4,778,815
[45] Date of Patent: Oct. 18, 1988

[54] METHOD OF INHIBITING CATARACTS BY TOPICAL APPLICATION OF A 2-SUBSTITUTED 1,2-BENZISOSELENAZOL-3(2H)-ONE

[75] Inventor: William D. Cash, Riverside, Conn.

[73] Assignee: Ciba-Geigy Corporation, Ardsley, N.Y.

[21] Appl. No.: 27,298

[22] Filed: Mar. 18, 1987

[51] Int. Cl.$^4$ .............................................. A61K 31/41
[52] U.S. Cl. ..................................... 514/359; 514/912
[58] Field of Search ................................. 514/359, 912

[56] References Cited

U.S. PATENT DOCUMENTS

| | | | |
|---|---|---|---|
| 4,352,799 | 10/1982 | Renson et al. | 424/244 |
| 4,397,858 | 8/1983 | Welter et al. | 424/270 |
| 4,418,069 | 11/1983 | Welter et al. | 548/100 |
| 4,454,068 | 6/1984 | Welter et al. | 260/239 R |
| 4,550,168 | 10/1985 | Welter et al. | 546/270 |
| 4,711,961 | 12/1987 | Welter et al. | 548/121 |

FOREIGN PATENT DOCUMENTS 44453 1/1982 European Pat. Off.
3616923 11/1987 Fed. Rep. of Germany.

OTHER PUBLICATIONS

Chem. Abst. 106:43,658v (1987)–Van Dyke et al.
Chem. Abst. 106:102,292w & 106:102293x (1987)–Welter et al.

*Primary Examiner*—Douglas W. Robinson
*Attorney, Agent, or Firm*—Irving M. Fishman

[57] ABSTRACT

A method of inhibiting cataract formation occasioned by the oxidative cross-linking of proteinaceous material in the lens fiber of the eye of a mammal comprising the topical administration of an effective antioxidant amount, to the eye of said mammal in need of the same, of a compound of the formula:

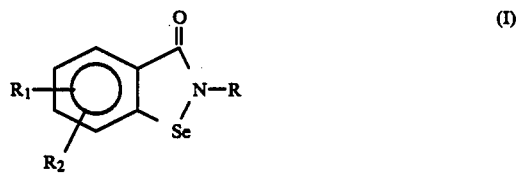

wherein
R is phenyl or phenyl substituted lower alkyl, the phenyl group of each being unsubstituted or substituted by halo, lower alkyl, lower alkoxy, trifluoromethyl, nitro, di-loweralkylamino, cyano, carboxy, methylenedioxy, loweralkoxycarbonyl, carboxyloweralkyl, or loweralkoxycarbonyl-lower alkyl, or R is cycloalkyl of 5 to 10 carbon atoms; and $R_1$ and $R_2$ are independently hydrogen, halo, lower alkyl, lower alkoxy, hydroxy, trifluoromethyl, or nitro or $R_1$ and $R_2$ taken together are methylenedioxy.

2 Claims, No Drawings

METHOD OF INHIBITING CATARACTS BY TOPICAL APPLICATION OF A 2-SUBSTITUTED 1,2-BENZISOSELENAZOL-3(2H)-ONE

BACKGROUND OF THE INVENTION

The instant invention relates to a method of inhibiting cataract formation occasioned by the oxidative cross-linking of proteinaceous material in the lens fiber of the eye of a warm-blooded mammal, including man, by topically applying an effective antioxidant amount of a 2-aryl, aralkyl or cycloalkyl-1,2-benzisoselenazol-3(2H)-one to the eye of said mammal in need of the same.

Cataracts are an especially common eye abnormality which generally occur in older mammals and characteristically result as a consequence of long term oxidative insult to the ocular environment. Such cataracts are sometimes called senile cataracts to distinguish the same from diabetic cataracts which may be occasioned by dulcitol accumulation in the lens. While a galactose free diet may inhibit or even reverse the cataractous changes associated with diabetes, senile cataracts cannot be so treated by diet modification. In senile type cataracts, cloudiness or opacity of the eye lens is generally occasioned by oxidative cross-linking of ocular proteinaceous material in the lens fiber.

The compounds useful in the practice of this invention belong to a known class of compounds which are disclosed as having anti-inflammatory properties, as see U.S. Pat. Nos. 4,352,799; 4,397,858; 4,418,069; and 4,454,068.

However, the use of the subject compounds for the purpose of inhibiting cataracts occasioned by oxidative cross-linking of proteinaceous material in the lens fiber of the eye of a mammal, such as classical senile cataracts, has not been described.

Accordingly, it is an object of the present invention to provide for a method of inhibiting cataract formation occasioned by cross-linking of proteinaceous material in the lens fiber of the eye.

It is a further object of the present invention to provide for a method of halting or retarding the rate cataract formation in mammals predisposed to the condition of senile cataracts by the topical application of such compounds.

It is yet a further object of the present invention to provide aqueous formulations which are compatable to the ocular environment for use in such methods.

These and other objects of the present inventions are apparent from the following specific disclosures.

DETAILED DESCRIPTION OF THE INVENTION

One embodiment of the present invention relates to a method of inhibiting cataract formation occasioned by the oxidative cross-linking of proteinaceous material in the lens fiber of the eye of a mammal, comprising the topical administration of an effective antioxidant amount, to the eye of said mammal in need of the same, of a compound of the formula:

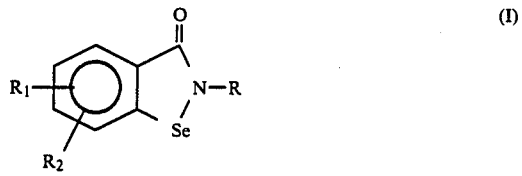

wherein
R is phenyl or phenyl substituted lower alkyl, the phenyl group of each being unsubstituted or substituted by halo, lower alkyl, lower alkoxy, trifluoromethyl, nitro, di-loweralkylamino, cyano, carboxy, methylenedioxy, lower alkoxycarbonyl, carboxyloweralkyl or lower alkoxycarbonyl substituted lower alkyl, or R is cycloalkyl of 5 to 10 carbon atoms; and $R_1$ and $R_2$ are independently hydrogen, halo, lower alkyl, lower alkoxy, hydroxy, trifluoromethyl or nitro, or $R_1$ and $R_2$ are adjacent and taken together are methylenedioxy.

Preferred are those compounds of formula I wherein R is said phenyl or substituted phenyl and $R_1$ and $R_2$ are hydrogen. Most preferred R is phenyl and $R_1$ and $R_2$ are hydrogen.

By "lower" as in lower alkyl, or lower alkoxy, etc. is meant alkyl of 1 to 4 carbon atoms, preferably 1 to 2 carbon atoms.

By "halo" is meant preferably chloro, bromo or fluoro, most preferably chloro.

The compounds can be prepared by methods known, per se. Thus, the compounds of formula I can be prepared by reacting a compound of the formula

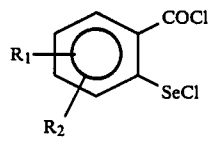

with an amine of the formula $R-NH_2$      III under conventional ring closure conditions, e.g. at a temperature between about −20° C. to about 20° C., optionally in the presence of an organic tertiary amine, such as a tri-lower alkyl amine such as triethylamine, or pyridine, in an inert diluent, such as tetrahydrofuran or carbon tetrachloride, and recovering the product.

The compounds of formula I and their preparation are more fully described in U.S. Pat. Nos. 4,352,799; 4,397,858; 4,418,069 and 4,454,068, the disclosures of which are incorporated herein.

Advantageously the compound of formula is topically administered to the eye in the form of an aqueous solution, suspension, ointment or cream or in the form of a controlled release lozenge or within a rate controlled membrane containing device for placement within the conjunctival sac. Preferably, the compound is administered in the form of an aqueous solution or suspension containing between about 0.002 to about 5 percent by weight, most preferably between about 0.004 and about 2% by weight, of a compound of formula I.

In order to enhance the solubility of the active agent of frmula I in the ocular composition, pharmaceutically acceptable eye compatable adjuvants, such as ethoxylated castor oil, propylene glycol, glycerine, low molecular weight polyethylene glycol, poloxamers and the like, in amounts between about 0.01 and about 30 weight percent, based upon the total weight of the composition, may be employed. Also, conventional pharmaceutical excipients, such as sodium borate, boric acid, tromethamine, potassium chloride, sodium phosphate, sodium citrate and the like may be present in amounts between about 0.01 and 3 weight percent, based upon the total weight of the composition. In addition, opthamologically acceptable preservatives, such as sodium edetate, benzalkonium chloride, sorbic acid and the like may be present in amounts between about 0.005 and about 0.1 weight percent, based upon the total weight of composition. If desired, the resulting composition osmolality may be adjusted, e.g. with sodium chloride or the like, such that the composition is substantially isotonic. Preferbly, the pH of the aqueous composition is between about 5 and about 7.

While not being bound by any specific mode of inhibition of oxidative cross-linking of proteinaceous material, it is believed that the compounds of formula I operate by inhibiting peroxide buildup in eye lens epithelial cells thus protecting such cells against oxidative stress.

The following Example is merely for illustrative purposes and is not intended to limit the invention. All parts are parts by weight unless otherwise indicated.

EXAMPLE 1

0.055 Mg of micronized 2-phenyl-1,2-benzisoselenazol-3(2H)-one, 50 grams of polyethoxylated high purity castor oil (Cremophor ® EL, BASF Wyandotte Corp ), 19 grams of boric acid and 0.75 grams of tromethamine are combined with sufficient water to provide one liter of solution. The solution has a pH of between 5.2 and 5.5 and contains the 2-phenyl-1,2-benzisoselenazol-3(2H)-one in a concentration of 0.2 micromolar. One to two drops of the solution (about 50 to about 100 microliters) can be placed into each eye of the mammalian host.

What is claimed is:

1. A method of inhibiting cataract formation occasioned by the oxidative cross-linking of proteinaceous material in the lens fiber of the eye of a mammal, comprising the topical administration of an effective antioxidant amount, to the eye of said mammal in need thereof, of a compound of the formula:

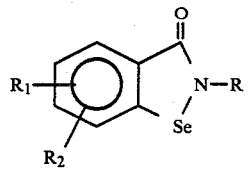

wherein
R is phenyl or phenyl substituted lower alkyl, wherein the phenyl group of each is unsubstituted or substituted by halo, lower alkyl, lower alkoxy, trifluoromethyl, nitro, di-lower alkylamino, cyano, carboxy, methylenedioxy, lower alkoxycarbonyl, carboxy substituted lower alkyl, or lower alkoxycarbonyl substituted lower alkyl, or R is cycloalkyl of 5 to 10 carbon atoms; and
$R_1$ and $R_2$ are independently hydrogen, halo, lower alkyl, lower alkoxy, hydroxy, trifluoromethyl or nitro, or $R_1$ and $R_2$ taken together are methylenedioxy.

2. A method according to claim 1 wherein R is phenyl and both $R_1$ and $R_2$ are hydrogen.

* * * * *